(12) United States Patent
Peterson et al.

(10) Patent No.: US 9,192,503 B1
(45) Date of Patent: Nov. 24, 2015

(54) MECHANICAL MASSAGE AND TRACTION APPARATUS

(71) Applicants: Peter W. Peterson, Franklin, TN (US); George H. Blaisdell, Graham, NC (US)

(72) Inventors: Peter W. Peterson, Franklin, TN (US); George H. Blaisdell, Graham, NC (US)

( * ) Notice: Subject to any disclaimer, the term of this patent is extended or adjusted under 35 U.S.C. 154(b) by 0 days.

(21) Appl. No.: 14/217,372

(22) Filed: Mar. 17, 2014

Related U.S. Application Data

(63) Continuation-in-part of application No. 13/176,739, filed on Jul. 5, 2011, now abandoned.

(60) Provisional application No. 61/801,574, filed on Mar. 15, 2013.

(51) Int. Cl.
*A61F 5/00* (2006.01)
*A61F 5/04* (2006.01)
*A61H 39/04* (2006.01)

(52) U.S. Cl.
CPC . *A61F 5/04* (2013.01); *A61H 39/04* (2013.01)

(58) Field of Classification Search
CPC .......... A61F 5/04; A61F 5/042; A61F 5/048; A63B 23/025; A63B 23/00; A61H 1/00; A61H 1/008; A61H 1/0292; A61H 2201/16; A61H 2201/1604; A61H 2201/1607; A61H 2201/1609; A61H 2201/1611; A61H 2201/1614; A61H 2201/1616; A61H 2201/1676; A61H 2203/0456; A61H 2205/02; A61H 2205/04

USPC .............. 602/32, 36, 35, 38, 39; 482/10, 122, 482/121, 123, 124, 907; 128/845, 848; 601/39, 84, 97, 134, 136, 5, 23, 98; 5/636, 640, 622, 944
See application file for complete search history.

(56) References Cited

U.S. PATENT DOCUMENTS 8,303,626 B2 * 11/2012 Fischer .......................... 606/241

* cited by examiner

*Primary Examiner* — Victoria J Hicks
(74) *Attorney, Agent, or Firm* — Albert W. Watkins

(57) ABSTRACT

A mechanical massage and traction apparatus provides patient weight-induced cervical traction and particular stimulation of distinct pressure points along a patient's shoulders and occipital ridge. A fixed base provides at least two shoulder-engaging members that preferably firmly engage with and massage the patient's shoulders. Pivotally coupled to the base is a head support that includes a plurality of occipital ridge engaging fingers that preferably firmly engage with and massage the patient's occipital ridge. A spring between the base and head support operatively flexes under the weight of the patient's head and shoulders, and thereby increases a distance between the shoulder-engaging members and occipital ridge support, to operatively produce traction in the patient's cervical vertebrae. The upper torso support operatively contacts an underlying support surface, and the occipital ridge support operatively floats above the underlying support surface.

6 Claims, 15 Drawing Sheets

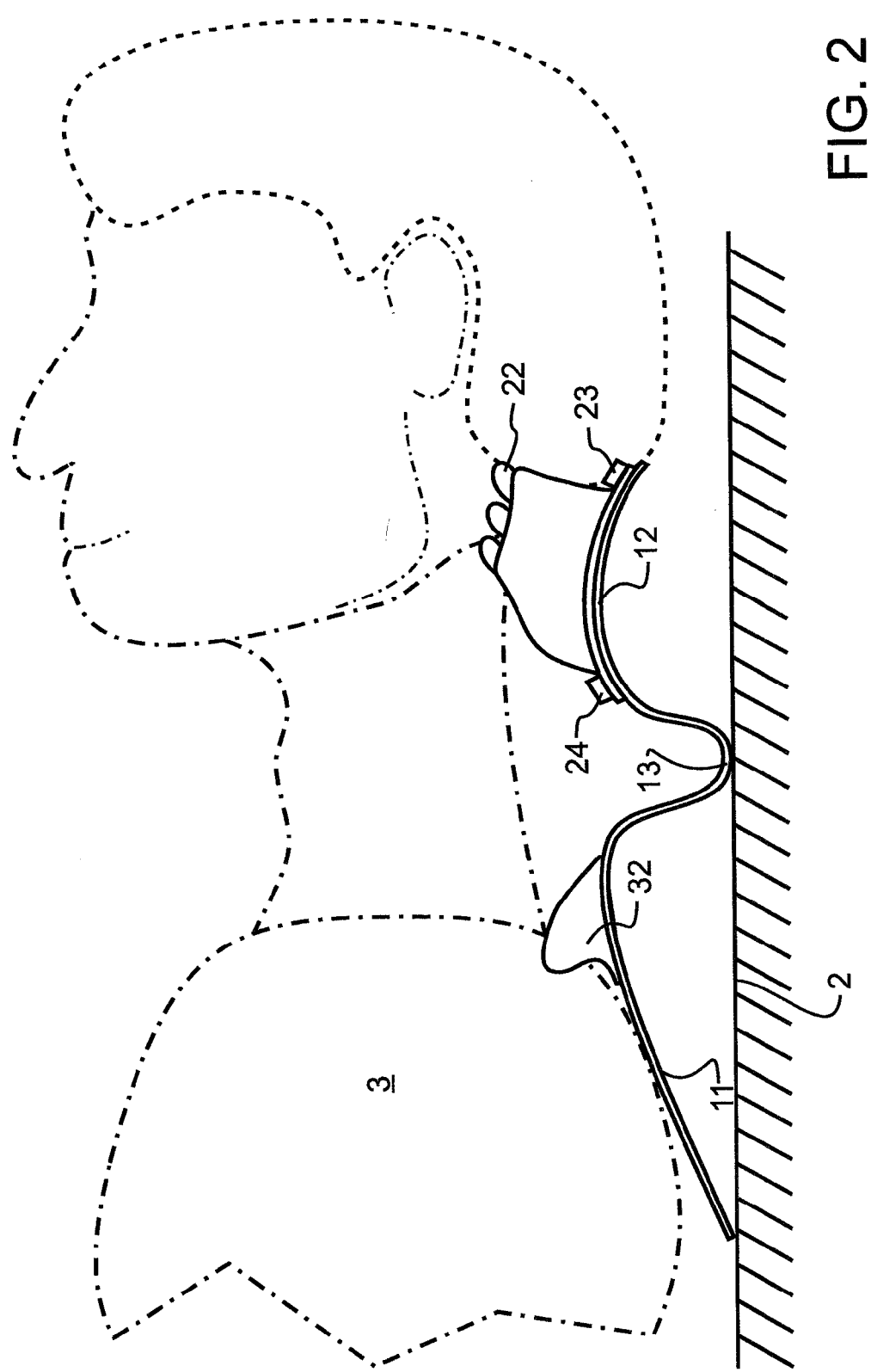

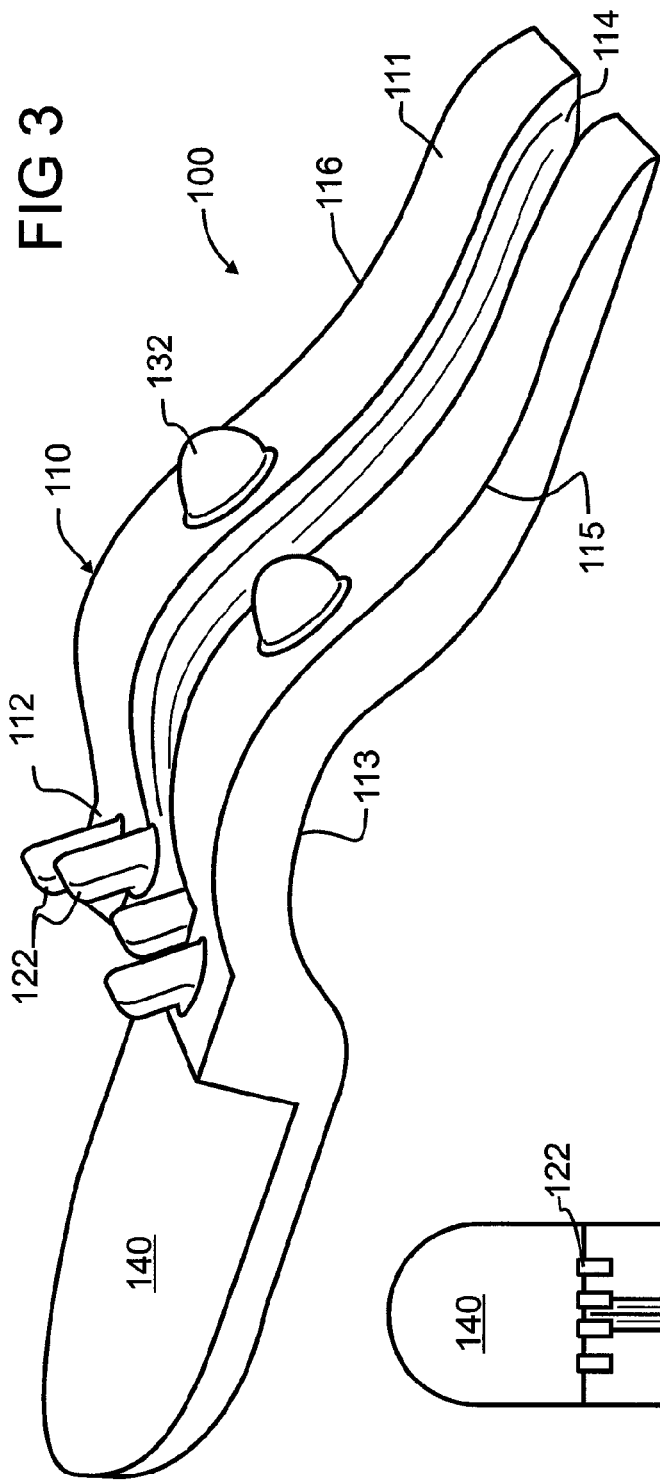
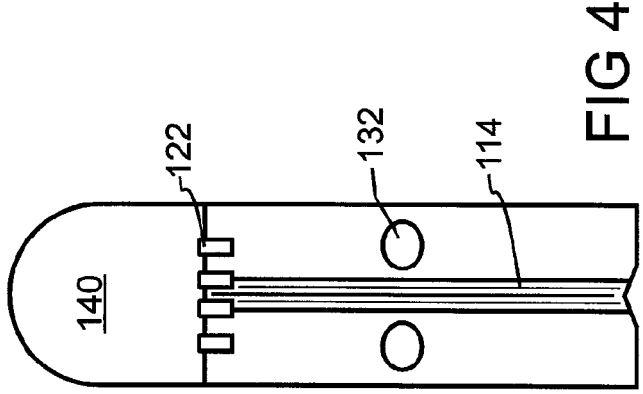

MECHANICAL MASSAGE AND TRACTION APPARATUS

CROSS REFERENCE TO RELATED APPLICATIONS

This application claims the benefit under 35 USC 119(e) of U.S. provisional 61/801,574, filed Mar. 15, 2013, and is a continuation-in-part of U.S. application Ser. No. 13/176,739 filed Jul. 5, 2011 and co-pending herewith, the contents of each incorporated herein by reference in entirety.

BACKGROUND OF THE INVENTION

1. Field of the Invention

This invention pertains generally to chiropractic or osteopathic implements for restoring or tending to restore a portion of the body to its normal position or to a more proper position, and more particularly to a positioner for a recumbent user comprising a formed element beneficial to the cervical spine when a patient lays supine upon the element.

2. Description of the Related Art

While the modern world provides many opportunities and benefits that did not exist in years past, the results of the changes that have occurred over the years are not always as beneficial as one might hope. While the modern world frees us from the dangers and unpredictability of the hunting and gathering lifestyle of our ancestors, which many people are quite grateful for, there are negative side effects that have come with the changes. One striking change is the general pace of life and pressures associated therewith, which leads to much stress in many individuals. Back in the days of our distant ancestors, adverse hormones produced during stress, such as cortisol, were worked off physically. The physical activity often restored the health and well-being of the individual. Unfortunately, the adverse health effects associated with what is often a more sedentary lifestyle, such as may be found in the confines of an office or cubicle, include such issues as a lack of or greatly reduced physical activity that could otherwise alleviate the adverse affects of stress and a seeming endless confinement to various chairs, seats and other body supports. This combination often leads to tension, knots, fatigue and other undesirable musculo-skeletal phenomena in many individuals.

While some individuals are fortunate enough to have recognized the benefits of the services of a masseuse or chiropractor to help them to relieve the tension and stress that accumulates within their bodies, such services are dependent upon the individual recognizing the need for help, being able to afford such help as frequently as required, and upon the skill and knowledge of the professional to be able to adequately provide the much needed physical treatment.

One such area where services are often required is in the treatment of the cervical vertebrae that define a person's neck. While proponents of evolution believe that man's evolution involved a transition from a hunched posture, modern man leaning over a keyboard, an assembly line, or even a workpiece in a machine shop seems to directly resemble that hunched posture. This puts substantial stress on a person's neck. Furthermore, many people tend to concentrate stress at various focal points within their body, and the cervical vertebrae are a common location. In addition, certain medical conditions such as cervical spondylosis and migraine headaches produce moderate to severe discomfort in the cervical region of the afflicted individual. Release of the occipital ridge is highly beneficial to proper chiropractic treatment or stress release. Finally, without the rigors of regular activity, even sudden movements of a person's head or sleeping in an awkward position can be sufficient to trigger pain, soreness, and tension in a person's neck.

The only currently widely-available effective treatments for neck pain require direct manual treatment or manipulation of the afflicted person. Such treatments require the full time and attention of a skilled masseuse or chiropractor. As a result, the masseuse or chiropractor is unable to tend to other patients in need during the provision of neck services, driving the costs for such treatments up, and, again, requiring not only diagnostic skill by the professional but also significant manual work.

A primary requirement of proper treatment of the cervical vertebrae is to provide gentle traction. This is a gentle pulling that tends to pull the vertebrae apart from each other, which is quite different from the ordinary compression that occurs throughout the day when a person is in a more upright position. This gentle pull permits fluids to flow in between skeletal components that are not otherwise as open to fluid passage. Traction can be beneficially applied to many musculo-skeletal ailments, but rarely will any relieve as much stress or bring as much relief and pleasure to a person as traction applied directly to the occipital ridge, which is at the back of the head where the base of the skull protrudes from the spine.

A number of artisans have heretofore recognized the benefits of cervical traction. Various patents and publications illustrating apparatus that incorporate pneumatic traction, the contents and teachings of each which are incorporated herein by reference, include: U.S. Pat. No. 5,441,479 by Chitwood, entitled "Cervical traction device"; U.S. Pat. No. 5,454,781 by Chitwood, entitled "Inflatable cervical traction/stretch device"; U.S. Pat. No. 5,569,176 by Graham, entitled "Inflatable cervical traction and exercising device"; U.S. Pat. No. 5,709,649 by Chitwood, entitled "Neck curvature alignment device"; U.S. Pat. No. 5,713,841 by Graham, entitled "Inflatable cervical cervico-thoracic thoraco-lumbar and lumbar exercising device"; and Chinese patent publication 201019888Y. While these devices are capable of providing relief to certain individuals in carefully controlled situations, there are a number of drawbacks associated with pneumatic devices. The first and most obvious drawback is the relative fragility of the apparatus, which is prone to accidental punctures and leaks. However, a second and potentially more serious drawback is the inability of an inexperienced user to accurately determine the appropriate amount of traction to generate, which creates the associated risk of too great or too little traction force being applied by the user of the apparatus. Pneumatic devices are capable of generating great forces with only relatively small pressure increases. In other words, a change of only one pound per square inch (PSI) in internal pressure, which is only one-fifteenth of ordinary atmospheric pressure, when applied across a ten to twenty square inch occipital ridge region will lead to ten to twenty pounds of force being applied thereto. Clearly, just a few pounds of internal pressure within the pneumatic device can undesirably lead to harmful forces being generated within the cervical region of the patient. Finally, owing to the necessary compliance of the pneumatic device, there is no real opportunity to generate increased patient application forces in selected specific regions while avoiding application forces in other specific regions.

Other artisans have illustrated mechanical traction apparatus, the contents and teachings of each which are incorporated herein by reference, including: U.S. Pat. No. 5,451,202 by Miller et al, entitled "Cervical traction device"; Chinese patent publication 2734181Y; Chinese patent publication 201253278Y; and Chinese patent publication 201119936Y.

While potentially more durable than the pneumatic counterparts, these mechanical apparatus suffer from similar risks in terms of a patient's ability to readily determine appropriate application forces.

Weight-induced traction can overcome the limitations regarding proper traction forces, if properly designed. Unfortunately, a surprising number of the prior weight-induced traction devices achieve traction simply by draping the body part over a domed or elevated member. This type of traction is of less benefit to a patient, owing to the necessary curvature of the spine about the support. Exemplary patents, the teachings and contents which are incorporated herein by reference, include: Chinese patent publication 2562676Y; Chinese patent publication 2868279Y; Chinese patent publication 201213643Y; Chinese patent publication 101574216A; and Chinese patent publication 2671449Y.

A few artisans have provided patents and publications that illustrate weight-induced traction that truly applies traction forces rather than simple gravitational forces developed about a simple curve. Exemplary patents that utilize differently angled fingers, which collapse in different directions when weight is applied thereto, the contents and teaching which are incorporated herein by reference, include: U.S. Pat. No. 4,383,342 by Forster, entitled "Mattress for a sitting or lying person"; U.S. Pat. No. 5,820,573 by Ramos, entitled "Body contour massage device and method"; and Japanese patent publication 2005288131A. The fingers used in these apparatus act simultaneously as a cushion and also to provide traction. However, since the fingers are relatively small and densely packed, the amount of maximum traction is quite limited, and the actual traction obtained is very subject to final positional movements by the patient. Consequently, predictable traction forces remain quite elusive. Additionally, these apparatus are extremely sensitive to proper patient positioning, and yet there is little to assist the patient with such positioning.

Two spring-loaded traction devices, the teachings and contents which are incorporated herein by reference, include Chinese patent publication 2870777Y and Chinese patent publication 2505048Y. While these pillows can be used to create a predictable amount of traction for a given weight load, these apparatus only provide engagement with the person's head, presumably depending upon the person resting upon a suitable surface. This means that the traction is unpredictably distributed throughout the person's vertebrae.

US published application 2007/0276438 by Meglin et al, the teachings and contents which are incorporated herein by reference, entitled "Back alignment device," provides massages transverse to a person's spine but provides no teachings for how this apparatus might be used for traction. Other patents and publications, the teachings and contents which are incorporated herein by reference, include: U.S. Pat. No. 5,445,647 by Choy, entitled "Spinal acupressure device"; U.S. Pat. No. 5,792,080 by Ookawa et al, entitled "Massaging apparatus having self-adjusting constant strength and non-adjust strength modes"; U.S. Pat. No. 6,485,443 by Garth, entitled "Seating products with self powered dynamic massage units"; US published application 2004/0064974 by Schuster, entitled "Mechanical support which can be arched, distorted, rotated and deformed"; Chinese patent publication 101455597A; Chinese patent publication 201085764Y; Chinese patent publication 201213896Y; and Chinese patent publication 2607120Y. In addition to the foregoing patents and publications, Webster's New Universal Unabridged Dictionary, Second Edition copyright 1983, is incorporated herein by reference in entirety for the definitions of words and terms used herein.

SUMMARY OF THE INVENTION

In a first manifestation, the invention is a mechanical massage and traction apparatus that provides a combination of cervical traction and particular stimulation of distinct pressure points along a patient's shoulders and occipital ridge. The apparatus has an upper torso support and an occipital ridge support. At least two shoulder engaging members are attached to and protrude from the upper torso support and are adapted to operatively firmly engage with a patient's shoulders. At least two occipital ridge engaging fingers are attached to and protrude from the occipital ridge support and are adapted to operatively firmly engage with a patient's occipital ridge. A pivot is located beneath the occipital ridge support and between the occipital ridge support and upper torso support. A spring between the upper torso support and occipital ridge support generates a force about the pivot urging the occipital ridge support closer to the upper torso support. When sufficient weight is operatively applied to the occipital ridge engaging fingers to overcome the force generated by the spring, the occipital ridge engaging fingers will move away from the upper torso support and thereby generate traction forces there between.

OBJECTS OF THE INVENTION

Exemplary embodiments of the present invention solve inadequacies of the prior art by providing a combination of cervical traction and particular stimulation of distinct pressure points along a patient's shoulders and occipital ridge. A fixed base provides shoulder-engaging members, and pivotally coupled to the base is a head support that includes a plurality of occipital ridge engaging fingers.

The present invention and the preferred and alternative embodiments have been developed with a number of objectives in mind. While not all of these objectives are found in or required of every embodiment, these objectives nevertheless provide a sense of the general intent and the many possible benefits that are available from ones of the various embodiments of the present invention.

A first object of the invention is to provide relief from improper or hunched posture, cervical spondylosis, cervical-muscular strains or knots, tension, and other undesirable cervical disorders or complications. A second object of the invention is to enable even an inexperienced user to safely establish an appropriate amount of traction. Another object of the present invention is for the apparatus to produce substantial and predictable traction that is primarily determined at the time of design, and that is independent of a surface upon which the patient and apparatus may rest. A further object of the invention is to facilitate automatic and proper patient positioning. Yet another object of the present invention is to provide body engaging members that are removable and replaceable for both adjustment for body size or dimension and also for repair or maintenance. An additional object of the present invention is to generate increased application forces in selected specific patient regions while avoiding application forces in other specific patient regions. Another object of the present invention is to provide an apparatus which meets the foregoing objectives while being durable, easily cleaned, and easily maintained.

BRIEF DESCRIPTION OF THE DRAWINGS

The foregoing and other objects, advantages, and novel features of the present invention can be understood and appreciated by reference to the following detailed description of the invention, taken in conjunction with the accompanying drawings, in which:

FIG. 2 illustrates the first preferred embodiment mechanical massage and traction apparatus of FIG. 1 from a side view and in further operative combination with a patient.

FIG. 3 illustrates a first alternative embodiment mechanical massage and traction apparatus from a projected view.

FIG. 4 illustrates the first alternative embodiment mechanical massage and traction apparatus of FIG. 3 from a top plan view.

DESCRIPTION OF THE PREFERRED EMBODIMENT

Various embodiments of apparatus designed in accord with the present invention have been illustrated in the various figures. The embodiments are distinguished by the hundreds digit, and various components within each embodiment designated by the ones and tens digits. However, many of the components are alike or similar between embodiments, so numbering of the ones and tens digits have been maintained wherever possible, such that identical, like or similar functions may more readily be identified between the embodiments. If not otherwise expressed, those skilled in the art will readily recognize the similarities and understand that in many cases like numbered ones and tens digit components may be substituted from one embodiment to another in accord with the present teachings, except where such substitution would otherwise destroy operation of the embodiment. Consequently, those skilled in the art will readily determine the function and operation of many of the components illustrated herein without unnecessary additional description.

Figure 1:
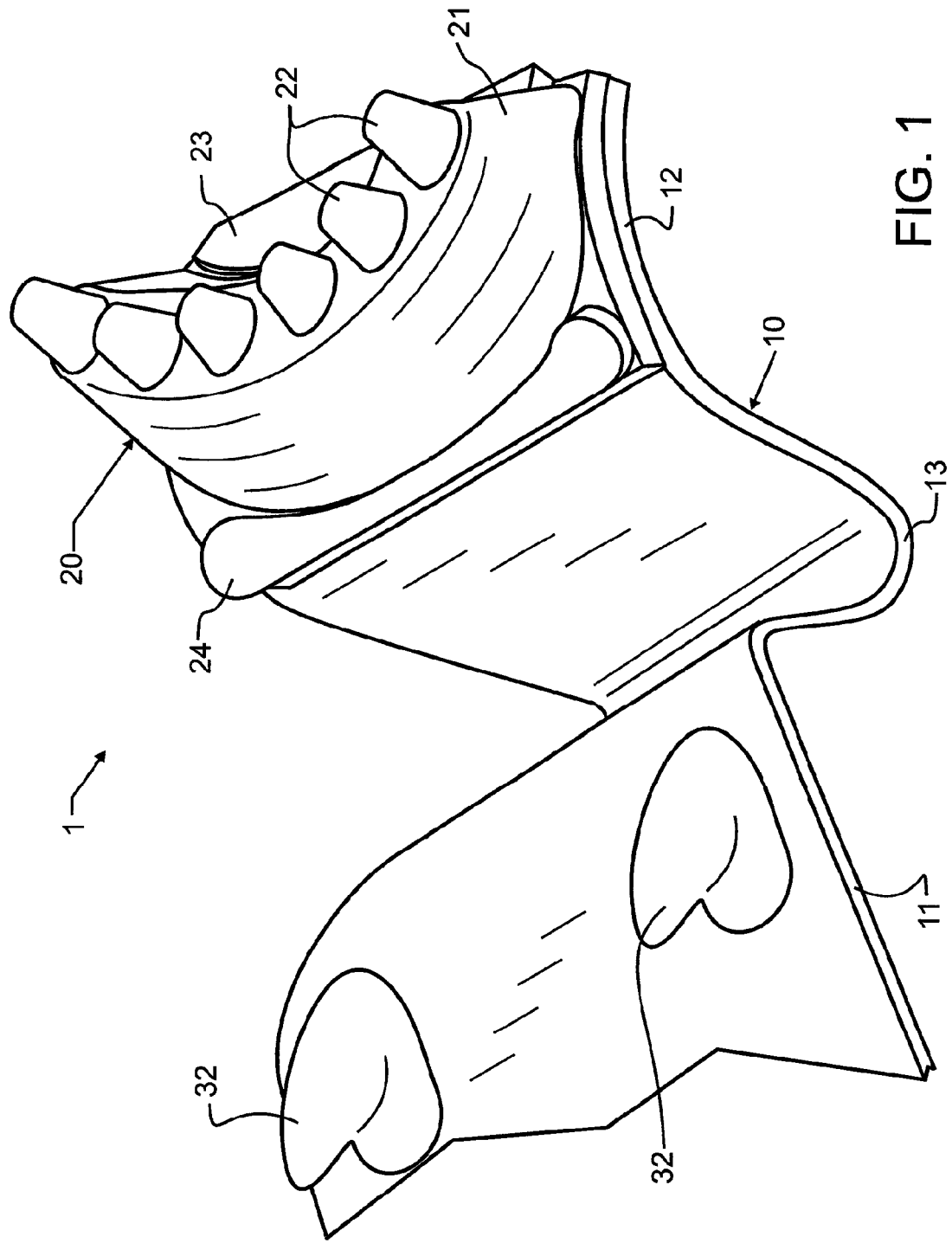
FIG. 1 illustrates a first preferred embodiment mechanical massage and traction apparatus designed in accord with the teachings of the present invention from an enlarged and projected view.

Manifested in the preferred embodiment, the present invention provides a combination of cervical traction and particular stimulation of distinct pressure points along a patient's shoulders and occipital ridge. FIGS. 1 and 2 illustrate a first preferred embodiment mechanical massage and traction apparatus 1. A wave-shaped spring member 10 has an upper torso support 11, an occipital ridge support 12, and a resilient wave-shaped spring 13 between upper torso support 11 and occipital ridge support 12. While resilient wave-shaped spring 13 is illustrated as forming a single U-shaped arc, it will be understood that more than one arc may be provided, and that a plurality of arcs resembling accordion pleating may be provided, as may be other known alternatives. Attached to upper torso support 11 and most preferably protruding therefrom are at least two shoulder engaging members 32 that are designed to operatively firmly engage with a patient's shoulders. Attached to occipital ridge support 12 and most preferably protruding therefrom is occipital ridge coupler 20 having at least one occipital support block 21 supported thereon with at least two occipital ridge engaging fingers 22. Occipital ridge engaging fingers 22 will most preferably be dimensioned and spaced to resemble the finger tips of a masseuse or chiropractor, such that a patient will receive selective and particular stimulation within the occipital ridge. Occipital ridge coupler 20 and shoulder engaging members 32 might be permanently coupled with or unitary with wave-shaped spring member 10. However, in preferred embodiment mechanical massage and traction apparatus 1, occipital ridge coupler 20 and shoulder engaging members 32 are removably engaged with wave-shaped spring member 10. While many different methods of attachment are contemplated herein and will be understood from the art of coupling, in preferred embodiment mechanical massage and traction apparatus 1, occipital ridge coupler 20 and shoulder engaging members 32 each preferably incorporate features that penetrate through and secure to wave-shaped spring member 10 in the manner of the notoriously well-known push pins used commonly in such applications as the fastening of automotive plastic body interior panels to metal body components. In the case of shoulder engaging members 32 as illustrated, each shoulder engaging member 32 will incorporate a push-pin feature. In the case of occipital ridge coupler 20, retaining strips 23, 24 may be provided that pass first through occipital support block 21 and then through and into secure engagement with occipital ridge support 12. Removably coupling occipital ridge coupler 20 and shoulder engaging members 32 to wave-shaped spring member 10, whether as shown and described in the preferred embodiment or through other known technique, enables occipital ridge coupler 20 and shoulder engaging members 32 to be removed and replaced for both adjustment for patient body size and dimension and also for repair or maintenance.

Wave-shaped spring member 10 is in the preferred embodiment fabricated from a formed planar sheet having relative rigidity along the planar axes, but, owing to the thinness compared to width and length, has relative resilience and flexure through the thickness. Other equivalent geometries may be used to accomplish this. Consequently, resilient wave-shaped spring 13 will flex under the weight of a person's head and shoulders and will tend to straighten out and return to a more nearly co-planar relationship with upper torso support 11 and occipital ridge support 12. As resilient wave-shaped spring 13 flattens, this will increase the distance between upper torso support 11 and occipital ridge support 12, thereby producing traction in the patient's cervical vertebrae. The magnitude of traction force is dependent upon a combination of the weight of the patient's torso, neck, and head and the rigidity of resilient wave-shaped spring 13. Consequently, larger patients will appropriately generate greater traction force than smaller patients. In addition, the simple formed sheet construction of wave-shaped spring member 10 provides durable construction that is easily cleaned and easily maintained.

As may be apparent, while upper torso support 11 and occipital ridge support 12 may be as rigid, or to a more limited degree resilient, as desired by a designer who will factor in comfort and other similar factors, the resilience of resilient wave-shaped spring 13 is preferably what controls the amount of traction produced for a given weight. With appropriate selection of materials and dimensions for wave-shaped spring member 10, even an inexperienced patient will safely establish an appropriate amount of traction simply by laying upon mechanical massage and traction apparatus 1. Furthermore, since occipital ridge support 12 may be designed to float above a support surface 2, if so desired, the amount of traction will remain independent of a surface upon which the patient 3 and apparatus may rest.

While shoulder engaging members 32 may be designed to cup around a patient's shoulders, more preferably they will selectively apply pressure at preferred points in the patient's shoulders while avoiding application forces in other specific patient regions and so may stimulate acupressure or similarly sensitive areas within the patient's shoulders. This is evident in FIG. 2, where the hook-shaped geometry presses into the patient's shoulders to selectively apply pressure at desired locations. Desirably, occipital ridge engaging fingers 22 will also selectively apply pressure at preferred points in the patient's occipital ridge while avoiding application forces in other specific patient regions. The combination of shoulder engaging members 32 and occipital ridge coupler 20 further ensure automatic and proper patient positioning immediately when the patient lays upon preferred mechanical massage and traction apparatus 1. An additional benefit arises from the patient's ability to rock from side to side (rotation about the spine) and through movements such as pushing down onto occipital ridge engaging fingers 22 to self-induce strengthening, massage and relief.

Preferred mechanical massage and traction apparatus 1 is designed in accord with the teachings of the present invention to provide many patients with immediate pain relief and stress release through the combination of cervical traction with proper pressure application through particular pressure points or means. Through the use of preferred mechanical massage and traction apparatus 1, the present invention provides relief to a patient with improper or hunched posture, cervical spondylosis, cervical-muscular strains or knots, tension, and other undesirable cervical disorders or complications. If further desired, a pillow or the like may be provided within the valley formed by resilient wave-shaped spring 13. Kyphosis, a pathology which involves a loss of the proper spinal curvature, may be treated with an appropriately shaped pillow to induce desired curvature in combination with the traction and applied pressure points of the present invention.

A first alternative embodiment mechanical massage and traction apparatus 100 illustrated in FIGS. 3 and 4 has a wave-shaped spring member 110 which has an upper torso support 111, an occipital ridge support 112, and a resilient wave-shaped spring 113. In operation, when a person lays upon mechanical massage and traction apparatus 100, resilient wave-shaped spring 113 will be driven down and flattened to more nearly contact an underlying floor or other support. Just as with resilient wave-shaped spring 13, this will generate traction within a patient's cervical vertebrae. Additional features found in mechanical massage and traction apparatus 100 include a central longitudinally running spinal depression 114 that accommodates a patient's spine therein, raised side edges 115, 116 that nestle the patient into proper position, at least two occipital ridge engaging fingers 122, at least two shoulder engaging members 132, and a head rest 140. Head rest 140 may include a pillow if so desired, and may further include a head strap extending therefrom, again if so desired, such as head strap 34 as illustrated in Chitwood U.S. Pat. No. 5,441,479 incorporated herein above by reference.

Figure 5:
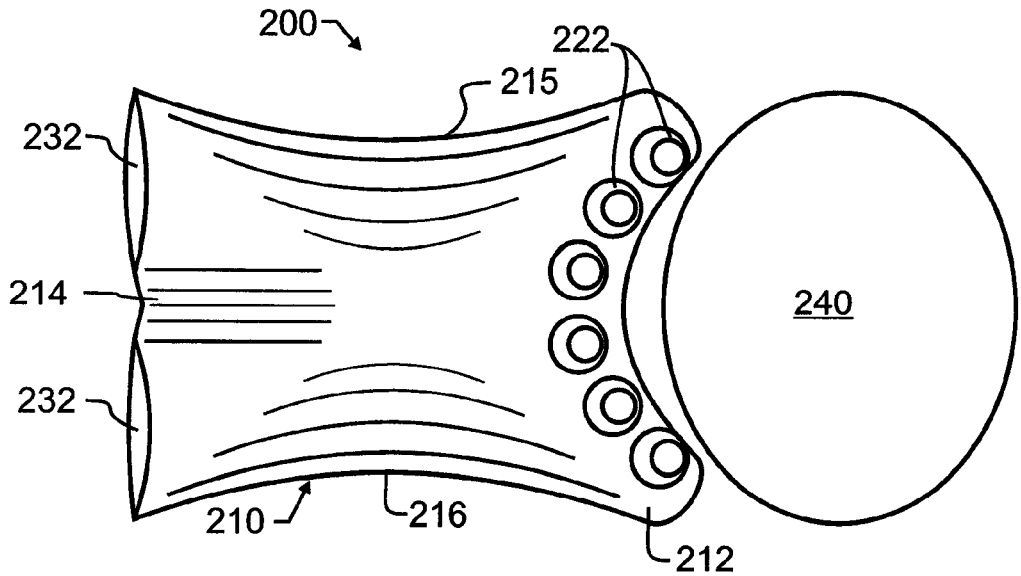
FIG. 5 illustrates a second alternative embodiment mechanical massage and traction apparatus from a top plan view.
Figure 6:
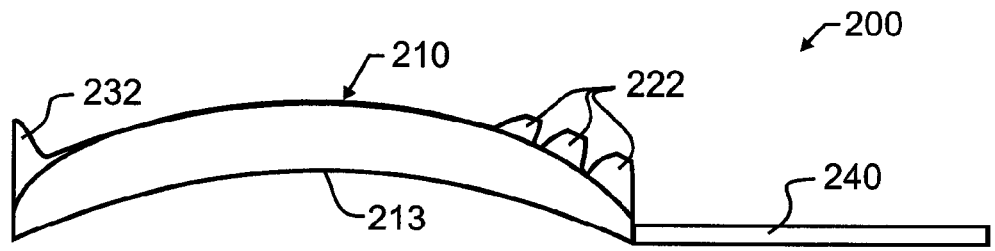
FIG. 6 illustrates the second alternative embodiment mechanical massage and traction apparatus of FIG. 5 from a side plan view.

A second alternative embodiment mechanical massage and traction apparatus 200 is illustrated in FIGS. 5 and 6. In this alternative embodiment, there is no upper torso support. Instead, two shoulder engaging members 232 are provided at one end of wave-shaped spring member 210 that wrap about the patient's shoulders. Distal thereto is an occipital ridge support 212 having at least two occipital ridge engaging fingers 222. A resilient wave-shaped spring 213 extends between shoulder engaging members 232 and occipital ridge support 212, which, similar to resilient wave-shaped spring 113, collapses when loaded, to thereby increase the distance between shoulder engaging members 232 and occipital ridge engaging fingers 222, to generate traction there between. A spinal depression 214 and raised side edges 215, 216 are provided, with similar function to spinal depression 114 and raised side edges 115, 116. Rather than an attached or integral headrest such as head rest 140, a separate head rest 240 may optionally be provided.

Figure 7:
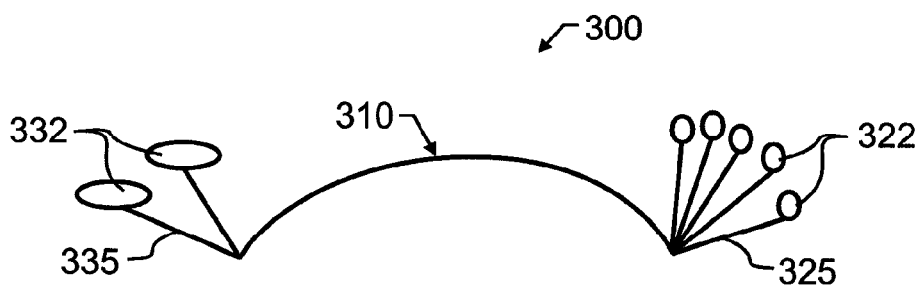
FIG. 7 illustrates a third alternative embodiment mechanical massage and traction apparatus from a side schematic view.
Figure 8:
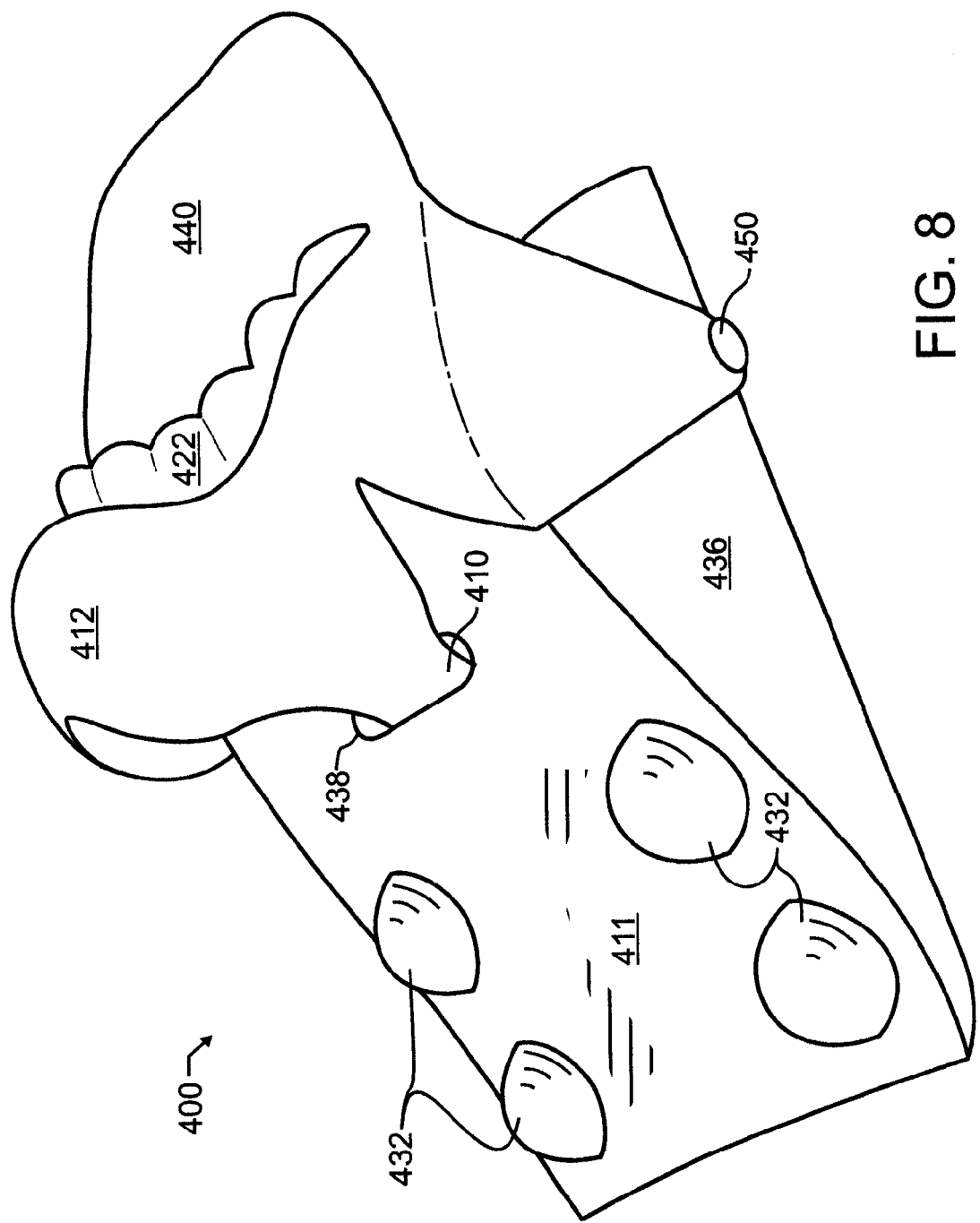
FIG. 8 illustrates a fourth alternative embodiment mechanical massage and traction apparatus from a perspective view.
Figure 9:
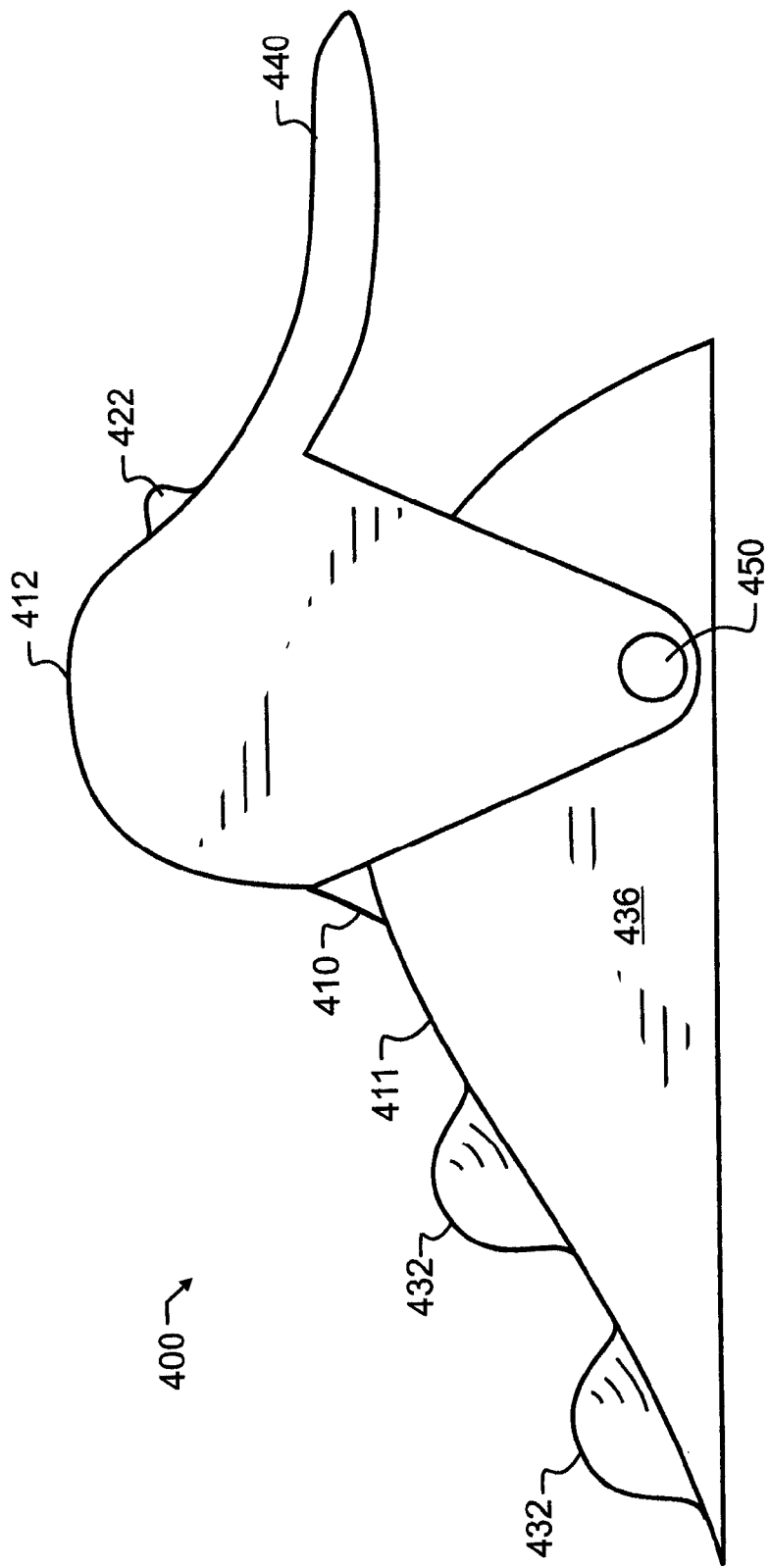
FIG. 9 illustrates the fourth alternative embodiment mechanical massage and traction apparatus of FIG. 8 from a side elevational view.
Figure 10:
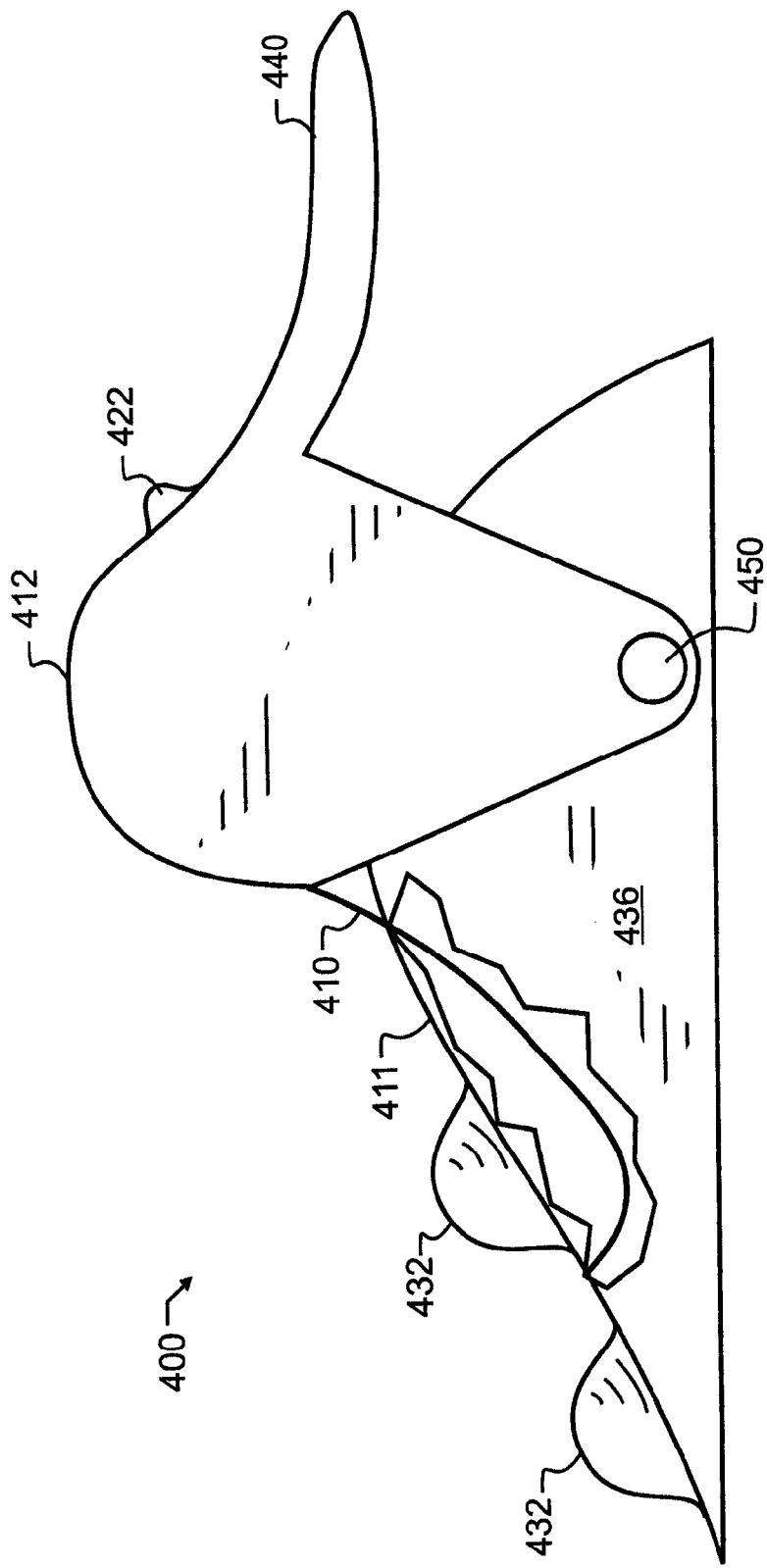
FIG. 10 illustrates the fourth alternative embodiment mechanical massage and traction apparatus of FIG. 8 from a side elevational view and illustrating the internal spring by partial cut-away view.
Figure 11:
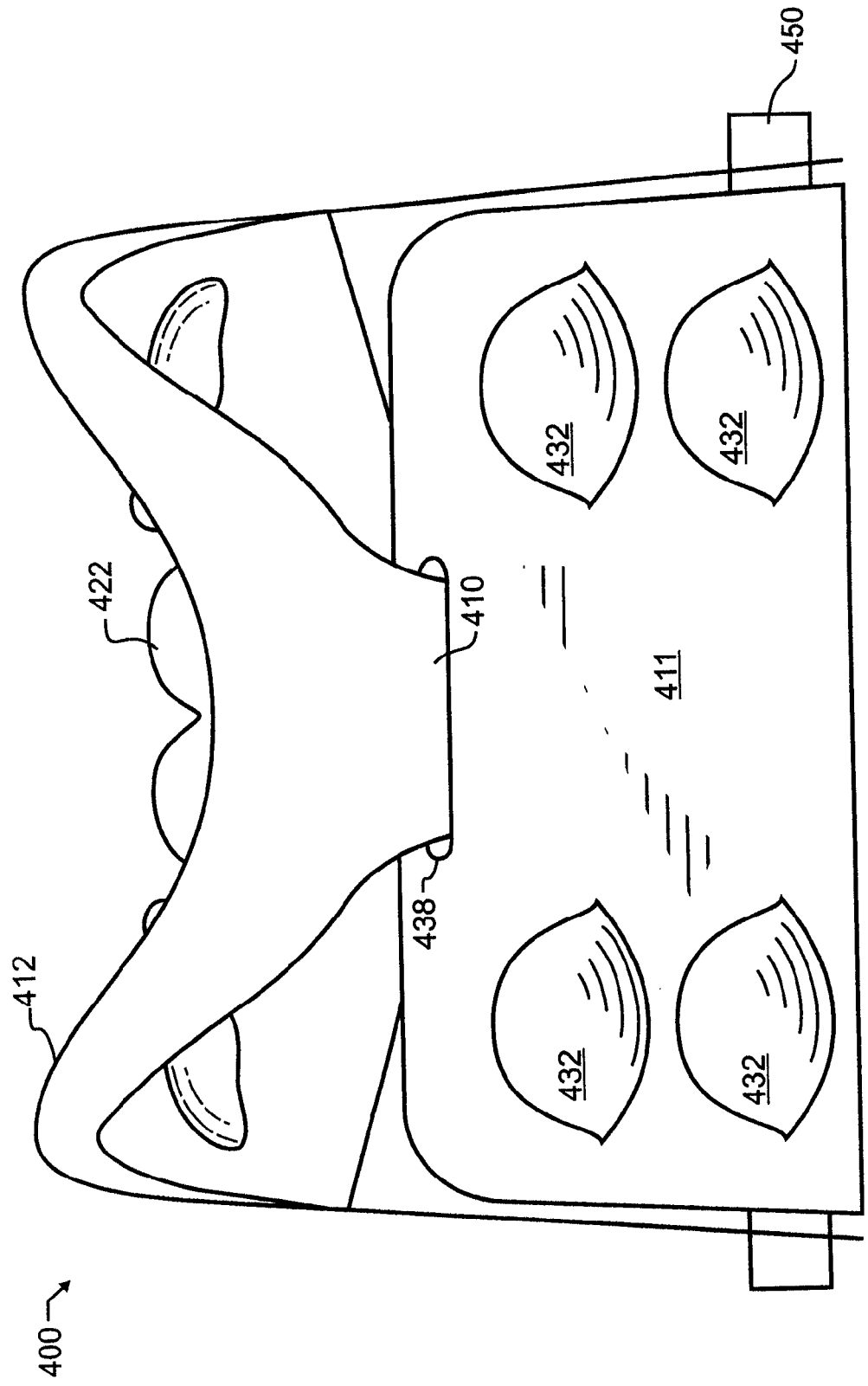
FIG. 11 illustrates the fourth alternative embodiment mechanical massage and traction apparatus of FIG. 8 from a left end view.
Figure 12:
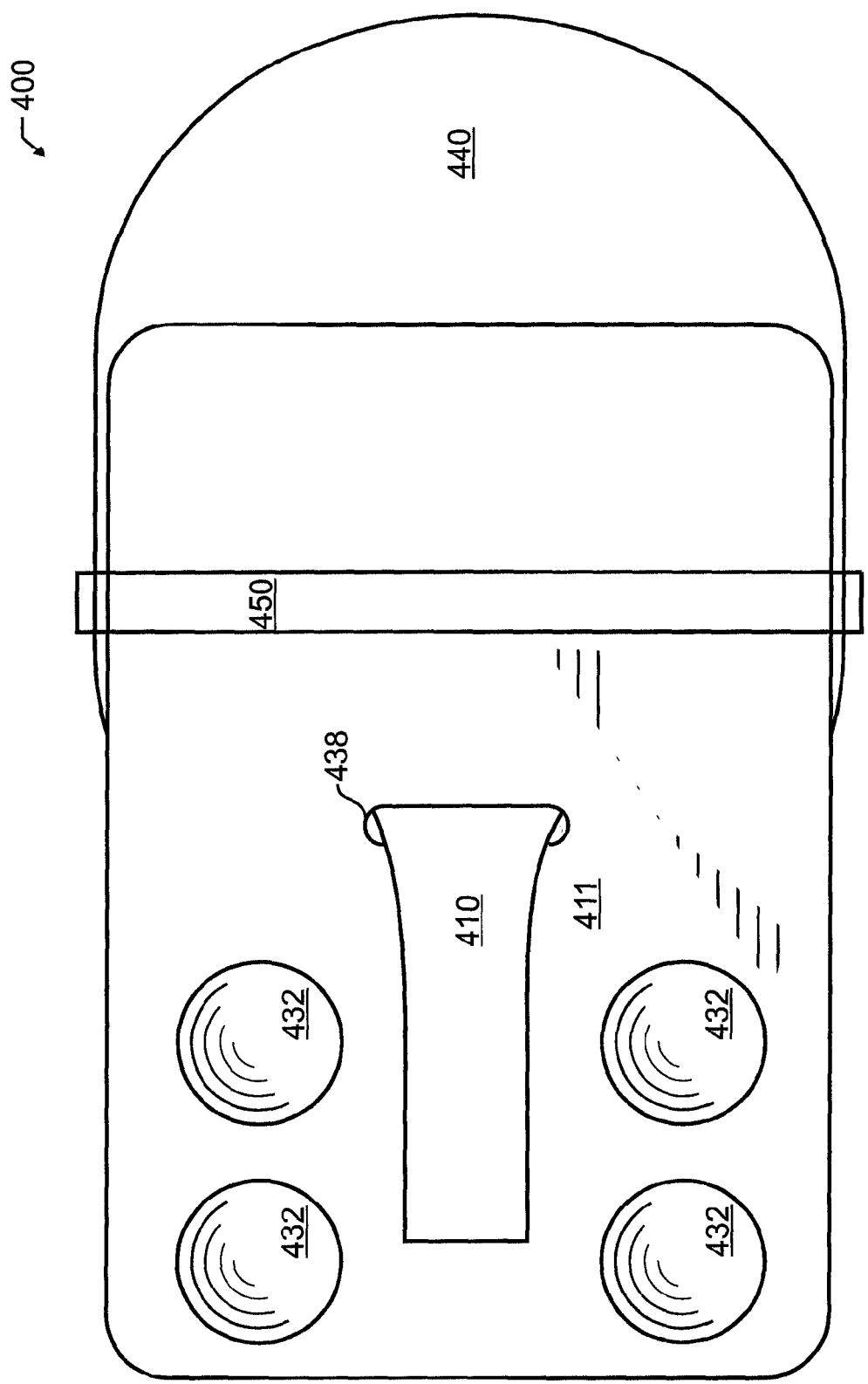
FIG. 12 illustrates the fourth alternative embodiment mechanical massage and traction apparatus of FIG. 8 from a bottom plan view.

FIG. 7 schematically illustrates a third alternative embodiment mechanical massage and traction apparatus 300 from a side schematic view, having a wave-shaped spring member 310 terminated at one end with at least two occipital ridge engaging fingers 322 and at the other distal end with at least two shoulder engaging members 332. The feature distinct to this third alternative embodiment is the further incorporation of resilient coupling links 325, 335. These resilient coupling links 325, 335 may provide earlier engagement with a patient than would occur with the previous embodiments. The exact amount of resilience in resilient coupling links 325, 335 will be decided upon by a designer at the time of fabrication of third alternative embodiment mechanical massage and traction apparatus 300, and this resilience can be used, if so desired, to further increase the total extension between occipital ridge engaging fingers 322 and shoulder engaging members 332. Alternatively, this additional resilience afforded by resilient coupling links 325, 335 may simply be used to add comfort or increase adaptability to patients of diverse body size.

A fourth alternative embodiment mechanical massage and traction apparatus 400 is illustrated from various views in FIGS. 8-14. In these Figures, the base and shoulder support 411, shoulder engaging members 432, and occipital ridge engaging fingers 422 supported upon occipital ridge support 412, are each functionally operative in the same manner as those of the previous embodiments. However, in this fourth alternative embodiment mechanical massage and traction apparatus 400, the base and shoulder support 411 and head rest 440 are pivotally coupled together through a pivotal connection 450 there between. In addition to pivotal connection 450, there is most preferably a slot 438 formed in base and shoulder support 411 that allows a spring 410 extending from head rest 440 to pass through slot 438. Most preferably, head rest 440 may be formed of relatively thinner plastic. Exemplary processes that might be used are vacuum forming of sheet or rotational molding, though any suitable fabrication process may be used. In accord with the teachings of the present invention, spring 410 is formed of a relatively thin, flexible and resilient material, whether integral with head rest 440 or otherwise coupled or attached thereto.

Figure 13:
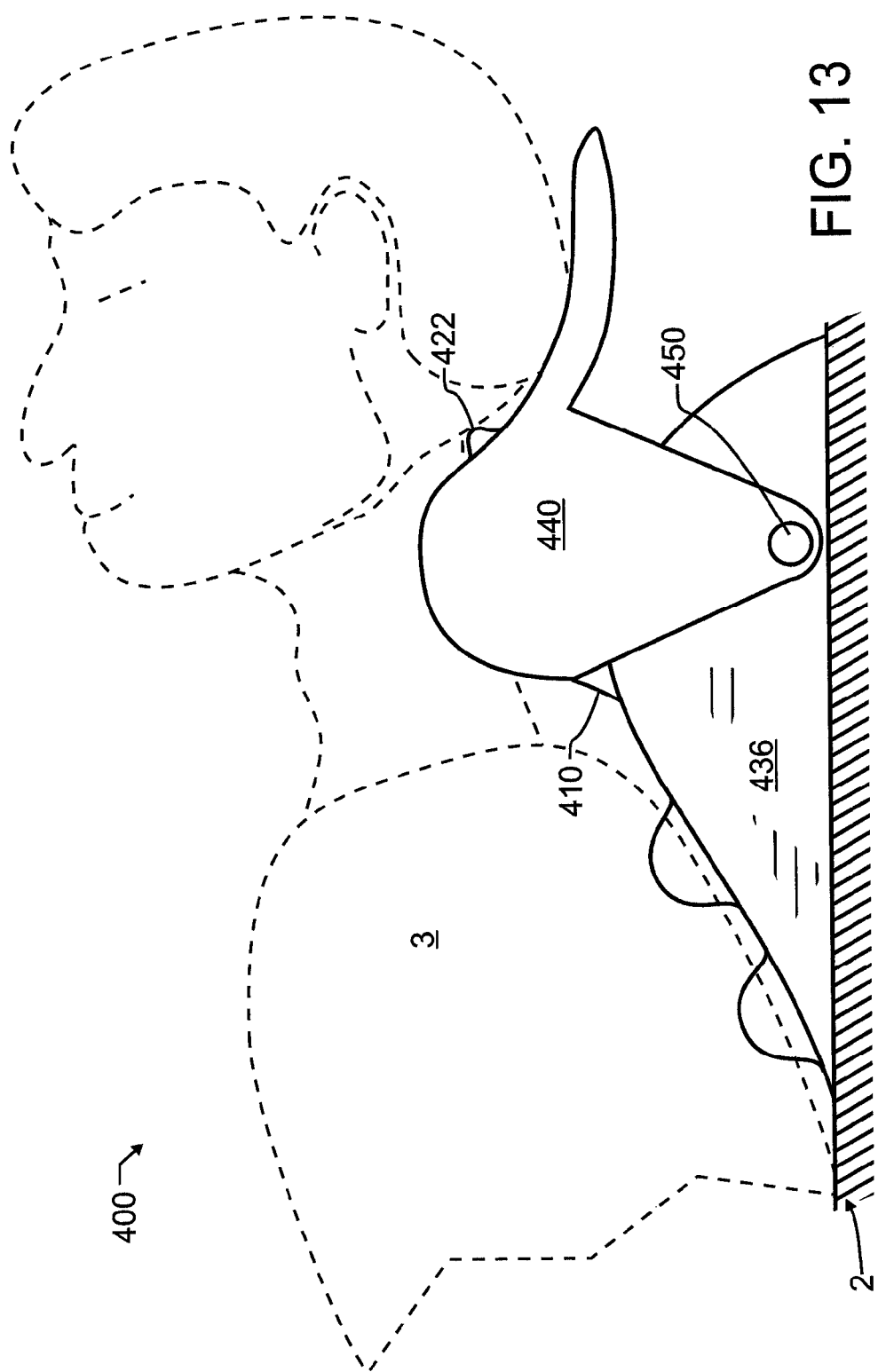
FIG. 13 illustrates the fourth alternative embodiment mechanical massage and traction apparatus of FIG. 8 from a side elevational view in further combination with a person, and just prior to the person fully resting their head thereupon.
Figure 14:
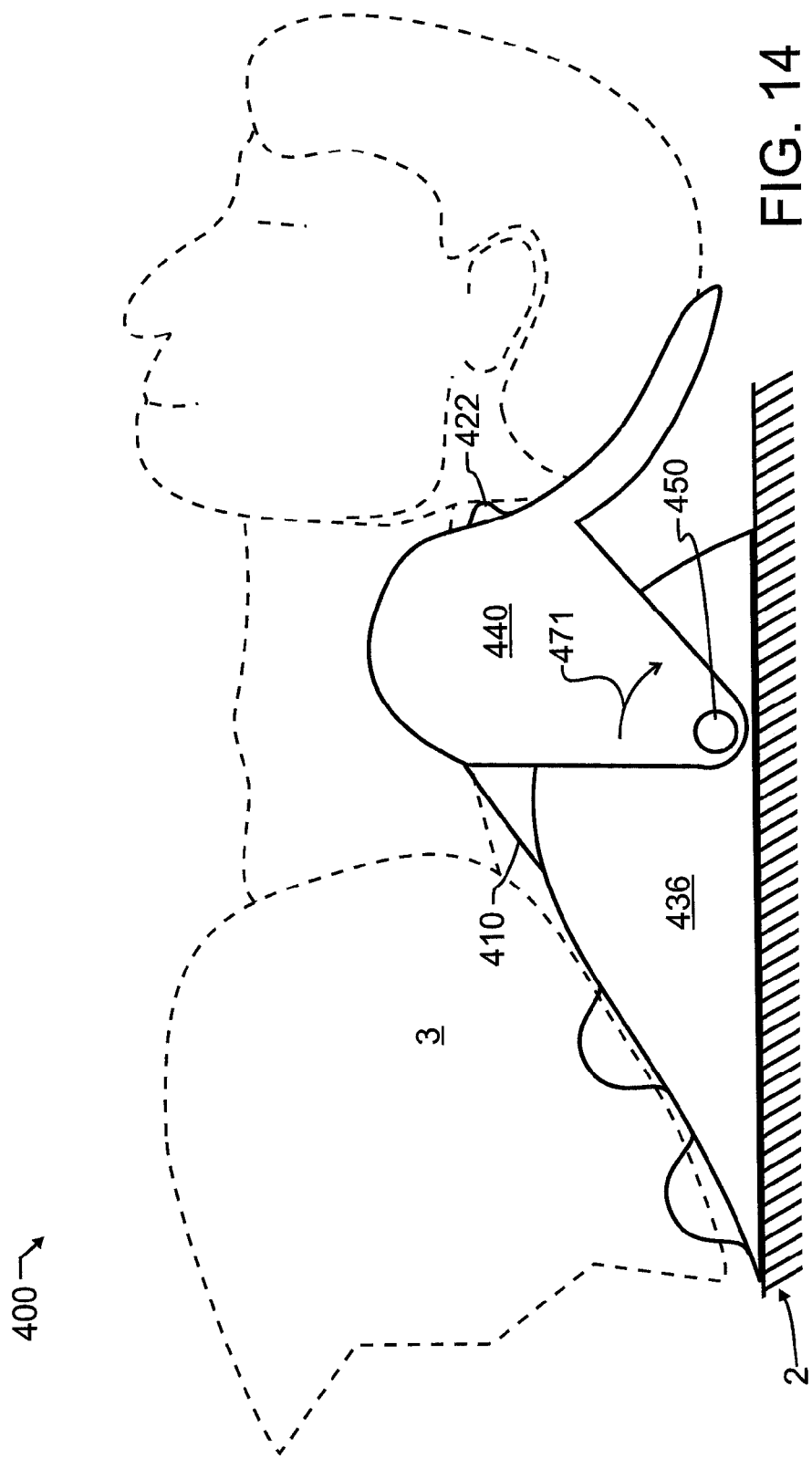
FIG. 14 illustrates the fourth alternative embodiment mechanical massage and traction apparatus of FIG. 8 from a side elevational view in further combination with a person, and subsequent to the person fully resting their head thereupon.

Referring to FIG. 13, when a person 3 begins to lay in a supine position upon the fourth alternative embodiment mechanical massage and traction apparatus 400, which in turn is resting upon a support surface 2 such as a floor, the ground, or other relatively flat or planar surface, spring 410 is relatively unloaded, only exhibiting slight flexure holding the end of spring 410 distal to head rest 440 against the inner top surface of base and shoulder support 411. This keeps head rest 440 in the elevated position shown in FIG. 13, until person 3 applies a force great enough to overcome the force of spring 410. When person 3 fully rests upon the fourth alternative embodiment mechanical massage and traction apparatus 400, spring 410 will be forced to flex, thereby allowing the person's head to lower to the position illustrated in FIG. 14. This rotation 471 of head rest 440 about pivotal connection 450 increases the distance between occipital ridge engaging fingers 422 and shoulder engaging members 432, thereby creating traction.

Figure 15:
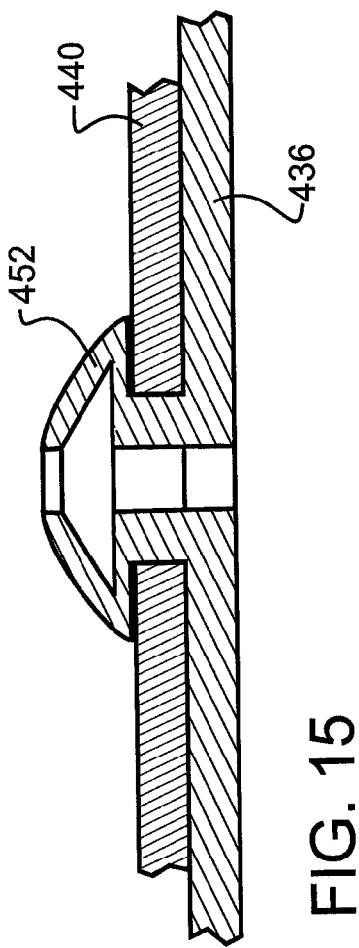
FIG. 15 illustrates an alternative embodiment pivotal coupling between the fixed shoulder-engaging base and the pivotal occipital ridge-engaging head support.

By forming head rest 440 and base and shoulder support 411 as illustrated, such as through rotational molding or vacuum thermoforming, fourth alternative embodiment mechanical massage and traction apparatus 400 may be formed from as little as two parts, each part formed in a single forming operation. In the illustrated embodiment, the pivotal connection 450 is formed by a shaft coupling the two parts, thereby resulting in three parts total. Nevertheless, and contemplated herein, a button 452 might alternatively be formed extending from the side wall 436 of base and shoulder support 411 and passing through a button hole in head rest 440 as illustrated in FIG. 15. By providing a button 452 or equivalent structure on each side wall 436 of base and shoulder support 411 where the pivotal connections 450 are illustrated in FIGS. 8-14, and by providing corresponding button holes in head rest 440, only two parts are required. Therefore, while the fourth alternative embodiment mechanical massage and traction apparatus is illustrated with a shaft 450 forming the pivotal connection and one further alternative button 452 is illustrated in FIG. 15, it will be understood that any other suitable pivotal connection as may be known in the mechanical arts is considered to be incorporated herein as well.

While spring 410 illustrated in FIGS. 8-14 is preferred owing to the ease of fabrication and assembly, and resistance to tangling or snagging of a person or their clothing, it will further be appreciated that other types of springs may be provided that urge head rest 440 up into the position illustrated in FIG. 13. These springs include tension, compression and looped springs, and any other suitable springs as are known in the mechanical arts, the use and installation into the fourth alternative embodiment mechanical massage and traction apparatus which will be apparent after a review of the present disclosure to those skilled in the mechanical arts.

Figure 16:
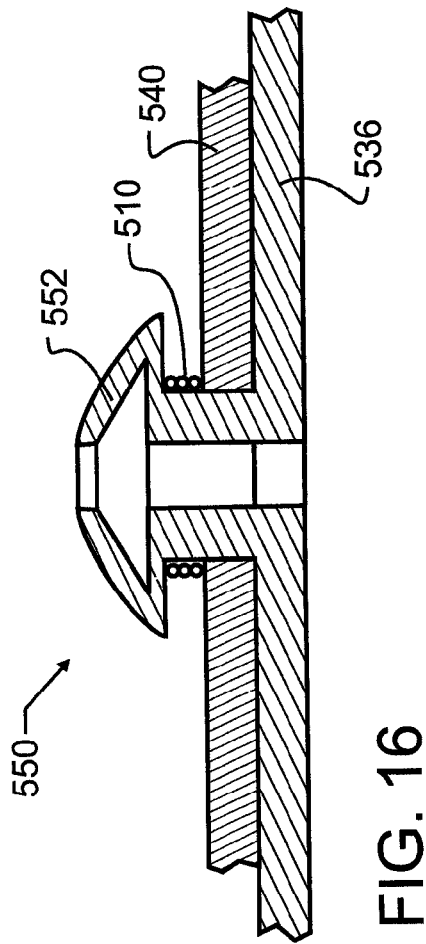
FIG. 16 illustrates a second alternative embodiment pivotal coupling between the fixed shoulder-engaging base and the pivotal occipital ridge-engaging head support that further incorporates a coil-type return spring.
Figure 17:
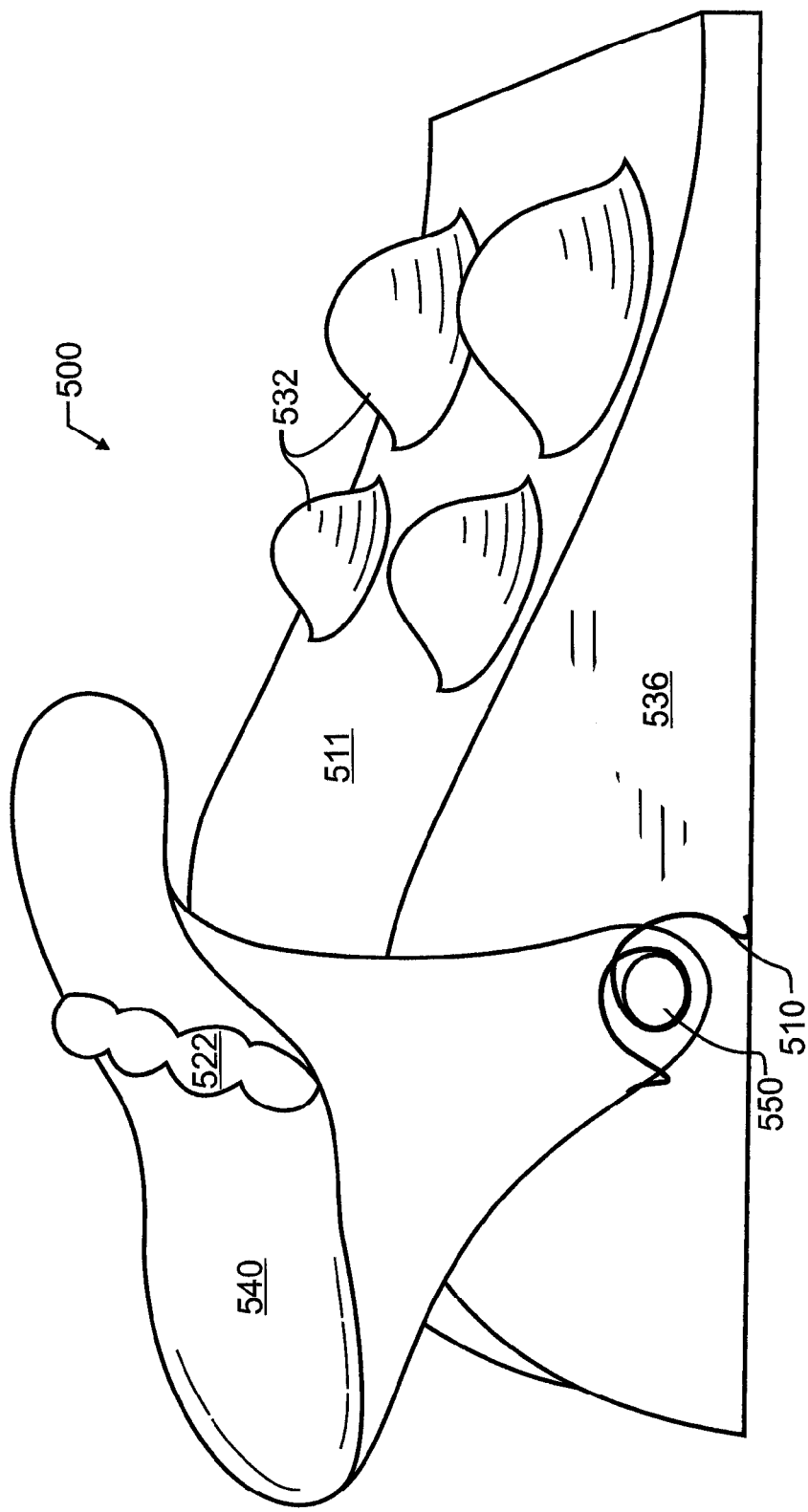
FIG. 17 illustrates a fifth alternative embodiment mechanical massage and traction apparatus from a perspective view.

Further examples are provided in FIGS. 16 and 17. FIG. 16 illustrates a second alternative embodiment pivotal coupling 550 defined by a button 552 similar to button 452, but having a longer shaft region about which a coil spring such as spring 510 may wrap. Spring 510 will preferably engage or be anchored adjacent a first end with the side wall 536 of fixed shoulder-engaging base and shoulder support 511 and pivotal head rest 540. In the embodiment illustrated in FIG. 16, the main body coils of spring 510 are wrapped interior of both pivotal head rest 540 and side wall 536. However, as illustrated in FIG. 17, fifth alternative embodiment mechanical massage and traction apparatus 500 may alternatively locate the main body coils of spring 510 exterior to both pivotal head rest 540 and side wall 536. In this case, as illustrated in FIG. 17, a shaft 550 will preferably be provided to couple base and shoulder support 511 with head rest 540. In yet another embodiment contemplated herein, the main body coils of spring 510 may be located between pivotal head rest 540 and side wall 536. The particular location of spring 510 may be varied in accord with the needs of a particular design.

One of the benefits provided by fifth alternative embodiment mechanical massage and traction apparatus 500 is the geometry of pivotal head rest 540. This geometry permits a cover to be applied in a manner similar to that of the well-known ironing board cover. In other words, and if so desired, the cover may have a draw string or the like that allows the underside to be drawn into and beneath the top surface. There are no parts extending from pivotal head rest 540 that would prevent the use of such a cover. Consequently, a removable cover may be readily used, and laundered at will.

Figure 18:
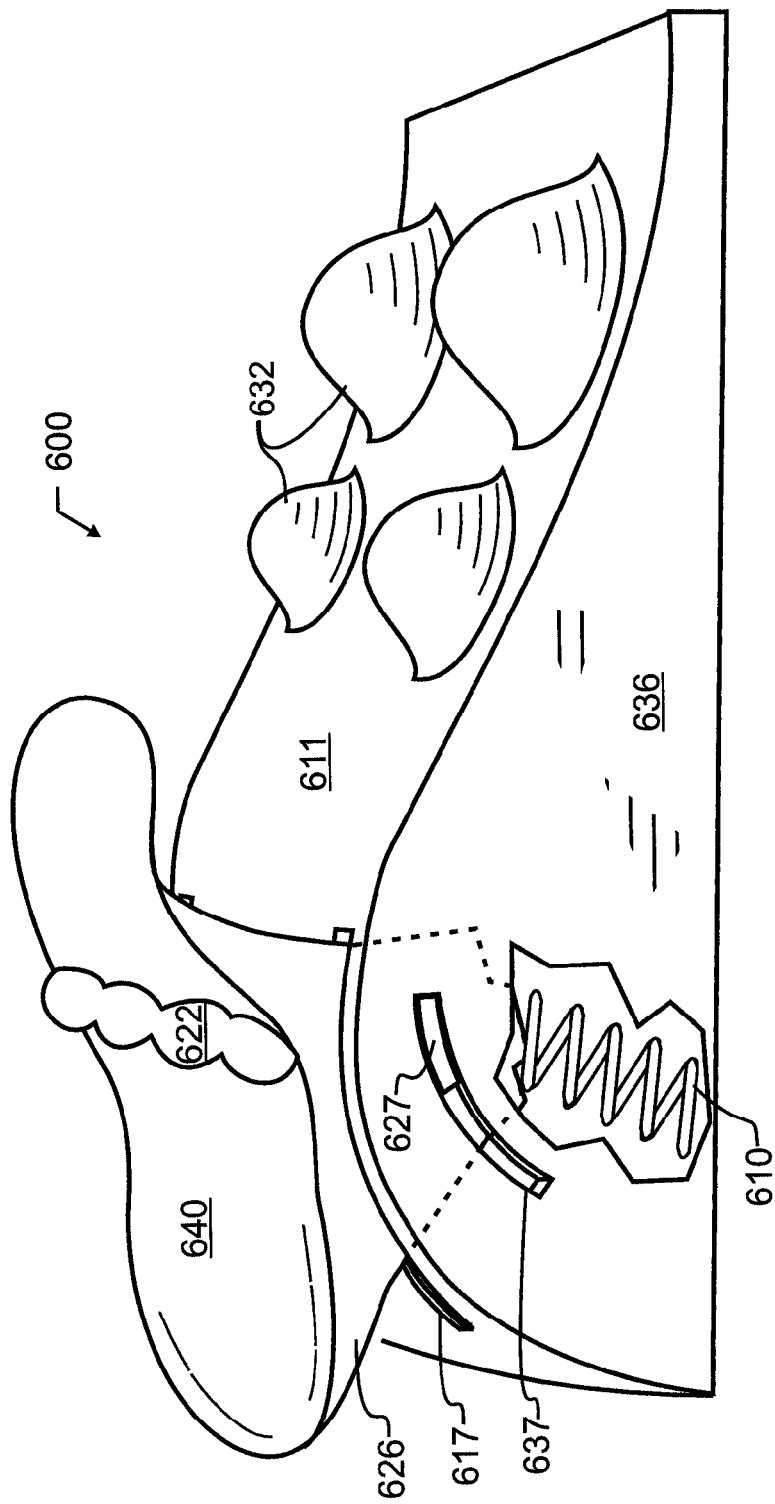
FIG. 18 illustrates a sixth alternative embodiment mechanical massage and traction apparatus from a perspective and partially cut-away view.

FIG. 18 illustrates a sixth alternative embodiment mechanical massage and traction apparatus 600 from a perspective and partially cut-away view. In this embodiment, head rest 640 has side wall 626 that are inserted internally of base and shoulder support 611 through slots 617, rather than exterior as in the earlier embodiments. Rather than providing a pivotal shaft, a pair of tracks 637 may be provided in side walls 636, and a pair of wings 627 extending normal to side walls 626 run in these tracks 637 to guide and control the rotation of head rest 640 relative to base and shoulder support 611. A cut-away of side wall 636 reveals a compression spring 610 therein which tends to push wing 627 to the position in tracks 637 illustrated in the Figure. Nevertheless, any type and location of spring which will bias head rest 640 in this position closest to shoulder engaging members 632 is suitable.

Figure 19:
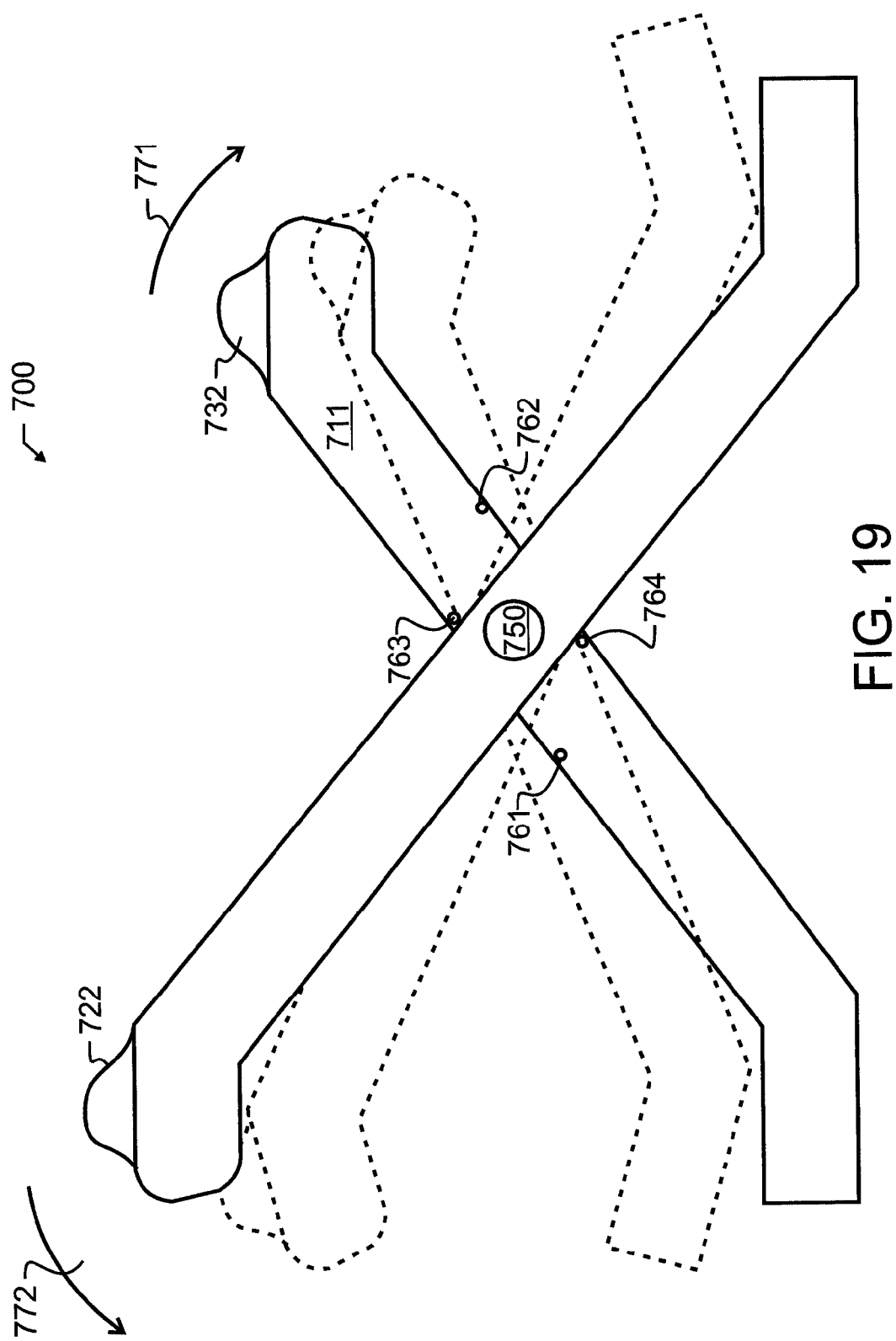
FIG. 19 illustrates a seventh alternative embodiment mechanical massage and traction apparatus from a side elevational view.

FIG. 19 illustrates a seventh alternative embodiment mechanical massage and traction apparatus 700 from a side elevational view. In this embodiment, a base and shoulder support 711 may be fabricated from a relatively planar sheet, having gentle bends at the ends thereof. To a first end the shoulder engaging members 732 may be formed or attached, and the end distal thereto will preferably act as a ground 2 engaging member. Midway between the ends a pivotal shaft 750 may be provided, and an occipital ridge support 712 may be journaled about pivotal shaft 750. The particular geometry of occipital ridge support 712 and base and shoulder support 711, when viewed from the top, orthogonally to FIG. 19, is not critical to the invention. Consequently, these two supports 711, 712 may be interleaved with each other similar to the two parts of a door or piano hinge, or one may run within a Y or notch cut in the other, such as occipital ridge support 712 running down an opening or notch formed generally centrally within base and shoulder support 711. While not illustrated, a spring will urge shoulder engaging members 732 towards occipital ridge engaging fingers 722. If the spring is a simple U-shaped resilient member, then the geometry of the spring alone may limit how closely shoulder engaging members 732 will come to occipital ridge engaging fingers 722. However, if a coil spring is used, then optional stops 763, 764 may be provided that protrude from base and shoulder support 711 in a manner that interferes with and thereby limits the rotation of occipital ridge support 712 relative thereto, and thereby ensures that, when unloaded, seventh alternative embodiment mechanical massage and traction apparatus 700 will be in the position illustrated by solid lines in FIG. 19. When a person rests their shoulders onto shoulder engaging members 732 and their occipital ridge onto occipital ridge engaging fingers 722, their body weight will induce rotation of base and shoulder support 711 and occipital ridge support 712 each about pivotal shaft 750. Base and shoulder support 711 will rotate in the direction of arrow 771, while occipital ridge support 712 will rotate in the direction of arrow 772. During this rotation, it is apparent that the ground engaging ends will have to slide upon a supporting surface 2. Optional stops 761, 762 may be provided to limit rotation to that shown by dashed lines in FIG. 19, regardless of the load applied. By counter-rotating the two supports 711, 712, the distance between shoulder engaging members 732 and occipital ridge engaging fingers 722 will increase, thereby inducing traction.

In each of the embodiments of FIGS. 8-19, the pivotal axis is below the occipital ridge engaging fingers and between the occipital ridge engaging fingers and the base and shoulder support. Consequently, when weight is applied to the head rest or occipital ridge engaging fingers, the occipital ridge engaging fingers will move away from the base and shoulder support, and thereby generate traction forces.

Suitable fabrication techniques enable components used in the preferred and alternative embodiments to be formed and sculpted to conform to a person's body, effectively guiding and "saddling" the person in place. While this may in many instances be sufficient, the apparatus may further be upholstered or finished in any other suitable or desirable way.

A mechanical massage and traction apparatus may be manufactured from a variety of materials, including metals, resins and plastics, ceramics or cementitious materials, or even combinations, composites or laminates of the above. The specific material used will be selected by a designer reasonably familiar with various materials and manufacturing processes.

While the foregoing details what is felt to be the preferred embodiment of the invention, no material limitations to the scope of the claimed invention are intended. Further, features and design alternatives that would be obvious to one of ordinary skill in the art are considered to be incorporated herein. The scope of the invention is set forth and particularly described in the claims herein below.

We claim:

1. A mechanical massage and traction apparatus that is adapted to operatively provide a combination of cervical traction and particular stimulation of distinct pressure points along a patient's shoulders and occipital ridge, comprising
   a base and shoulder support adapted to operatively rest upon a support surface and support said patient's shoulders above and spaced from said support surface;
   at least two shoulder engaging members attached to and protruding from said base and shoulder support and adapted to operatively firmly engage with a patient's shoulders;
   an occipital ridge support;
   at least two occipital ridge engaging fingers attached to and protruding from said occipital ridge support adapted to operatively firmly engage with a patient's occipital ridge;
   a pivot beneath said occipital ridge support and between said occipital ridge support and said base and shoulder support; and
   a spring between said base and shoulder support and said occipital ridge support and generating a force about said pivot urging said occipital ridge support closer to said base and shoulder support;
   whereby, when sufficient weight is operatively applied to said at least two occipital ridge engaging fingers to overcome said force generated by said spring, said at least two occipital ridge engaging fingers will move away from said base and shoulder support and thereby generate traction forces there between.

2. The mechanical massage and traction apparatus of claim 1, wherein said occipital ridge support operatively floats above said underlying support surface such that a magnitude of generated traction force is independent of said underlying support surface.

3. The mechanical massage and traction apparatus of claim 1, wherein said at least two shoulder engaging members are adapted to operatively selectively apply pressure at preferred points in said patient's shoulders while avoiding application forces in other specific patient regions, and so operatively stimulate sensitive areas within said patient's shoulders.

4. The mechanical massage and traction apparatus of claim 1, wherein said at least two shoulder engaging members further comprise a hook-shaped geometry.

5. The mechanical massage and traction apparatus of claim 1, wherein said at least two occipital ridge engaging fingers are adapted to operatively selectively apply pressure at preferred points in said patient's occipital ridge while avoiding application forces in other specific patient regions.

6. The mechanical massage and traction apparatus of claim 1, wherein said at least two shoulder engaging members are adapted to operatively wrap about said patient's shoulders.

* * * * *